United States Patent [19]

Evans

[11] Patent Number: 4,877,824

[45] Date of Patent: Oct. 31, 1989

[54] SULFUR-CONTAINING COMPOUNDS AS ANTIOXIDANTS FOR LUBRICANTS AND ELASTOMERS

[75] Inventor: Samuel Evans, Marly, Switzerland

[73] Assignee: Ciba-Geigy Corporation, Ardsley, N.Y.

[21] Appl. No.: 302,053

[22] Filed: Jan. 25, 1989

Related U.S. Application Data

[63] Continuation of Ser. No. 173,841, Mar. 28, 1988, abandoned.

[30] Foreign Application Priority Data

Apr. 8, 1987 [CH] Switzerland ............... 1351/87

[51] Int. Cl.$^4$ ............... C08K 5/47; C08K 5/36; C07C 149/243; C07D 249/10; C07D 241/46; C07D 219/62; C07D 209/86
[52] U.S. Cl. ............... 524/83; 524/89; 524/238; 524/239; 524/240; 252/47; 544/38; 544/347; 546/104; 548/444; 560/16; 560/110; 560/154; 560/250; 560/251; 560/253
[58] Field of Search ............... 524/83, 89, 238, 239, 524/240; 544/38, 347; 546/104; 548/444; 560/16, 110, 154, 250, 251, 253; 564/440; 252/47

[56] References Cited

U.S. PATENT DOCUMENTS

| 1,836,702 | 12/1931 | Christmann | 524/89 |
|---|---|---|---|
| 2,094,467 | 9/1937 | Reed | 524/83 |
| 2,282,710 | 5/1942 | Reppe et al. | 548/444 |
| 2,351,409 | 6/1945 | Dickey et al. | 564/440 |
| 2,397,960 | 4/1946 | Gribbins et al. | 252/47 |
| 2,657,982 | 11/1953 | Hill et al. | 562/427 |
| 2,998,405 | 8/1961 | Weldy | 252/47 |
| 3,014,888 | 12/1961 | Shimmin et al. | 524/83 |
| 3,352,882 | 11/1967 | Caldo et al. | 524/89 |
| 3,494,886 | 2/1970 | Tholstrup et al. | 524/83 |
| 3,803,140 | 4/1974 | Cook et al. | 524/83 |
| 3,912,727 | 10/1975 | Daniels | 260/243 |
| 4,430,452 | 2/1984 | Buysch et al. | 544/32 |
| 4,565,834 | 1/1986 | Buysch et al. | 544/38 |
| 4,608,399 | 8/1986 | Buysch et al. | 544/35 |
| 4,785,095 | 11/1988 | Salomon | 544/38 |

FOREIGN PATENT DOCUMENTS

| 38758 | 10/1981 | European Pat. Off. |
| 50-158638 | 12/1975 | Japan . |
| WO88/02007 | 3/1988 | PCT Int'l Appl. |

OTHER PUBLICATIONS

C. M. Murphy et al.-"Mode of Action of Phenothiazine Type Antioxidants", Ind. & Eng. Chem. 42, 2479-2489 (Dec. 1950).

Primary Examiner—Veronica P. Hoke
Attorney, Agent, or Firm—Stephen V. O'Brien

[57] ABSTRACT

Compounds of the formula (I)

$$R^1\!\!-\!\!\underset{R^2}{\overset{}{N}}\!\!-\!\!(CHR)_a\!\!-\!\!SR^3 \quad (I)$$

in which the Rs independently of one another are H, phenyl, naphthyl or $C_7$-$C_{30}$alkaryl and $R^1$ is H, $C_1$-$C_8$alkyl, $C_7$-$C_9$aralkyl, $C_5$-$C_{12}$cycloalkyl, phenyl, naphthyl, $C_7$-$C_{30}$alkaryl or a group of the formula (II)

$$-(CH_2)_a\!\!-\!\!SR^3 \quad (II)$$

$R^2$ is $C_7$-$C_{30}$alkaryl, phenyl, naphthyl or phenyl containing, in the para-position, an HO or $C_1$-$C_{18}$alkoxy group or a group of the formulae $$-N\!\!\underset{(CH_2)_a\!-\!SR^3}{\overset{R^4}{\diagup}} \quad \text{or}$$

$$-B\!\!-\!\!\underset{}{\underset{}{\bigcirc}}\!\!-\!\!N\!\!\underset{(CH_2)_a\!-\!SR^3}{\overset{R^1}{\diagup}} \quad \text{or} \quad -N\!\!\underset{H}{\overset{R^4}{\diagup}}$$

or $R^1$ and $R^2$, together with the nitrogen atom to which they are attached, are a radical of the formula (III)

$$R^5\!\!-\!\!\underset{}{\underset{}{\bigcirc}}\!\!-\!\!X\!\!-\!\!\underset{}{\underset{}{\bigcirc}}\!\!-\!\!R^5 \quad (III)$$

$R^3$ is a radical of the formulae —$(CH_2)_b$—$COOR^6$ or —$(CH_2)_2OCOR^7$, a is the number 1, 2 or 3 and b is the number 1 or 2, and $R^4$ is phenyl or a group of the formula (II), the two $R^5$s independently of one another are H, $C_1$-$C_{24}$alkyl, $C_5$-$C_{12}$cycloalkyl or $C_7$-$C_9$aralkyl, and $R^6$ is H, $C_1$-$C_{18}$alkyl or benzyl, $R^7$ is $C_1$-$C_{14}$alkyl, phenyl or a group of the formula $$-(CH_2)_m\!\!-\!\!Y\!\!-\!\!(CH_2)_m\!\!-\!\!COO(CH_2)_2\!\!-\!\!S\!\!-\!\!(CH_2)_aN(R^1)(R^2)$$

in which Y is —O— or —S—, a is the number 1, 2 or 3 and m is the number 1 or 2, B is a direct bond, —S—, —S—S— or a $C_1$-$C_{12}$alkylene radical, X in the formula (III) is a direct bond, —S— or a group of the formulae $$-\underset{R^9}{\overset{R^8}{\underset{|}{\overset{|}{C}}}}- \quad \text{or} \quad \underset{}{\overset{}{\diagdown}}\!\!N\!\!-\!\!(CH_2)_a\!\!-\!\!SR^3$$

form a phenothiazine, phenazine, acridine or carbazole radical.

8 Claims, No Drawings

SULFUR-CONTAINING COMPOUNDS AS ANTIOXIDANTS FOR LUBRICANTS AND ELASTOMERS

This application is a continuation of application Ser. No. 173,841, filed Mar. 3/28/88, now abandoned.

The present invention relates to novel sulfur-containing compounds, a process for their preparation and their use for stabilizing lubricants, hydraulic fluids and elastomers.

The stabilization of lubricants and elastomers with antioxidants, such as sterically hindered phenols, p-phenylenediamines or diphenylamine derivatives, has already been known for a long time. Diphenylamines or phenothiazines substituted on the nitrogen atom are also known as antioxidants and are described, for example, in German Offenlegungsschrift 2,228,350 or in EP patent application No. 70,436.

It has been found that amine derivatives containing a thioglycollic acid, thiopropionic acid or thioethoxy radical attached to the nitrogen atom are particularly suitable for stabilizing lubricants and hydraulic fluids, and also elastomers, and have outstanding properties as antioxidants.

Accordingly, the present invention relates to compounds of the formula I

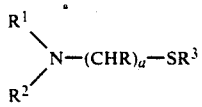
(I)

in which the Rs independently of one another are H, phenyl, naphthyl or $C_7$-$C_{30}$alkaryl and $R^1$ is H, $C_1$-$C_8$alkyl, $C_7$-$C_9$aralkyl, $C_5$-$C_{12}$cycloalkyl, phenyl, naphthyl, $C_7$-$C_{30}$alkaryl or a group of the formula (II)

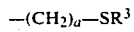
(II)

$R^2$ is $C_7$-$C_{30}$alkaryl, phenyl, naphthyl or phenyl containing an HO or $C_1$-$C_{18}$alkoxy group or a group of the formulae

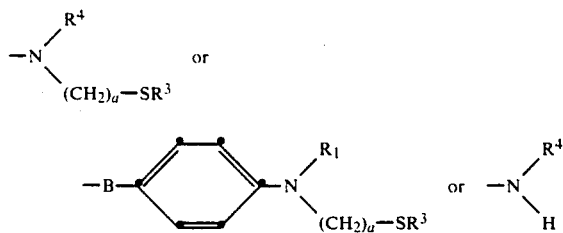

in the para-position, or $R^1$ and $R^2$, together with the nitrogen atom to which they are attached, are a radical of the formula (III)

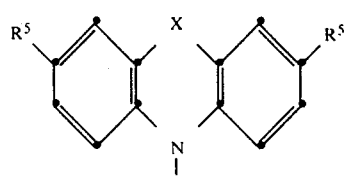
(III)

$R^3$ is a radical of the formulae —$(CH_2)_b$—$COOR^6$ or —$(CH_2)_2OCOR^7$, a is the number 1, 2 or 3 and b is the number 1 or 2, and $R^4$ is phenyl or a group of the formula (II), the two $R^5$s are independently of one another are H, $C_1$-$C_{24}$alkyl, $C_5$-$C_{12}$cycloalkyl or $C_7$-$C_9$aralkyl, and $R^6$ is H, $C_1$-$C_{24}$alkyl or benzyl, $R^7$ is $C_1$-$C_{14}$alkyl, phenyl or a group of the formula

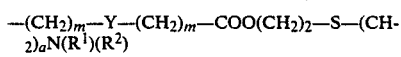

in which Y is —O— or —S—, a is the number 1, 2 or 3 and m is the number 1 or 2, B is a direct bond, —S—, —S—S— or a $C_1$-$C_{12}$alkylene radical, X in the formula (III) is a direct bond, —S— or a group of the formulae

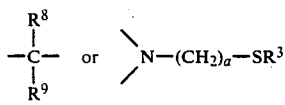

in which a and $R^3$ are as defined above, and $R^8$ and $R^9$ independently of one another are H, $C_1$-$C_8$alkyl or phenyl.

$R^1$, $R^8$ and $R^9$ as $C_1$-$C_8$alkyl are linear or branched alkyl groups, for example methyl, ethyl, n-propyl, isopropyl, n-butyl, tert-butyl, tert-amyl, n-hexyl, n-octyl and 1,1,3,3-tetramethylbutyl.

Examples of $C_1$-$C_{14}$alkyl as $R^7$ are the same alkyl groups have already been indicated above for the meaning of alkyl in $R^1$, $R^8$ and $R^9$, and also n-decyl, n-dodecyl and n-tetradecyl.

Examples of $R^1$ and $R^5$ as $C_7$-$C_9$aralkyl are benzyl, α-methylbenzyl or α,α-dimethylbenzyl.

As $R^1$ and $R^5$, $C_5$-$C_{12}$cycloalkyl is, for example, cyclopentyl, cyclohexyl, cycloheptyl, cyclooctyl and cyclododecyl.

Examples of R, $R^1$ and $R^2$ as alkaryl having 7 to 30 carbon atoms are phenyl which is substituted by one or two linear or branched alkyl groups having at least 1 C atom, or naphthyl which is substituted by one or two linear or branched alkyl groups having at least 1 C atom, the total number of C atoms in the alkyl group(s) being not more than 24 (if R, $R^1$ and $R^2$ are phenyl) and 20 (if R, $R^1$ and $R^2$ are naphthyl). Examples of alkyl groups are methyl, ethyl, propyl, isopropyl, n-butyl, isobutyl, tert-amyl, n-hexyl, 1,1,3,3-tetramethylbutyl, n-octyl, 2-ethylhexyl (isooctyl), n-decyl, n-dodecyl, n-tridecyl, n-tetradecyl, n-hexadecyl, n-octadecyl and n-eicosyl.

Examples of $C_1$-$C_{18}$alkyl or $C_1$-$C_{24}$alkyl as $R^6$ or $R^5$, respectively, are the same alkyl groups which have already been indicated above for the meaning of alkyl substituents in R, $R^1$ and $R^2$ as alkaryl. The preferred alkyl for $R^6$ is $C_1$-$C_{16}$alkyl, particularly $C_4$-$C_{16}$alkyl and very particularly $C_8$-$C_{14}$alkyl.

The preferred alkyl for $R^5$ is alkyl having 1-12, in particular 4-8 and very particularly 8, C atoms.

In $R^2$ representing phenyl substituted by a $C_1$-$C_{18}$ alkoxy group, the alkoxy group is, for example, methoxy, ethoxy, propoxy, isopropoxy, n-butoxy, isobutoxy, n-hexyloxy, n-octyloxy, n-decyloxy, n-dodecyloxy and n-octadecyloxy.

In the formula III the two radicals $R^5$ can be identical or different, but particularly identical.

As $C_1$-$C_{12}$alkylene, B is linear or branched radicals, for example methylene, ethylene, 1,2-propylene, 1,3- propylene, 1,2-, 1,3- or 1,4-butylene, 1,5-pentylene, 2-methyl-1,3-propylene, 1,6-hexylene, 1,7-heptylene, 1,2- or 1,8-octylene and 1,10-decylene.

Compounds which are preferred in accordance with the invention have the formula (I) in which R is H and $R^1$ is H, $C_1$-$C_{18}$alkyl, $C_7$-$C_{18}$alkaryl, cyclohexyl, phenyl, naphthyl or a group of the formula (II)

$$-(CH_2)_a-SR^3 \quad (II)$$

$R^2$ is $C_7$-$C_{18}$alkaryl, phenyl, napthyl or phenyl containing, in the paraposition, an HO group or a group of the formula

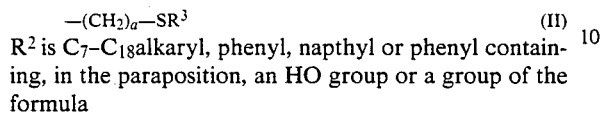

$R^1$ and $R^2$, together with the nitrogen atom to which they are attached, are a radical of the formula (III) above, $R^3$ is a radical of the formula —(CH$_2$)$_b$—COOR$^6$, a is the number 1 or 3 and b is the number 1 or 2, $R^4$ is phenyl or a group of the formula —(CH$_2$)$_a$—S(CH$_2$)$_b$—COOR$^6$ in which a and b are as defined above and $R^6$ is $C_1$-$C_{24}$alkyl, and, in the formula (III), the two $R^5$s are H, $C_1$-$C_{12}$alkyl or $C_9$phenylalkyl and X is —S—. As $R^1$ and $R^2$, naphthyl is β-naphthyl and especially α-naphthyl.

$C_9$phenylalkyl is, for example, α,α-dimethylbenzyl or α-methyl-β-phenylethyl.

Compounds of the formula (I) which are particularly preferred have the formula (I) in which R is H, $R^1$ is H, CH$_3$, C$_6$H$_5$, cyclohexyl, phenyl substituted by C$_4$-C$_{12}$alkyl, or a group of the formula —CH$_2$—S—CH$_2$—COOR$^6$, and $R^2$ is C$_6$H$_5$, naphthyl or phenyl substituted by C$_4$-C$_{12}$alkyl, or $R^1$ and $R^2$, together with the nitrogen atom to which they are attached, form a radical of the formula (III) above, a is the number 1, $R^3$ is a radical of the formula —CH$_2$COOR$^6$ and $R^6$ is C$_4$-C$_{18}$alkyl, and, in the formula (III), the two $R^5$s are H or C$_4$-C$_8$alkyl and X is —S—.

Examples of C$_4$-C$_{12}$alkyl as a sustituent for phenyl in $R^1$ and $R^2$ are n-butyl, /isobutyl, tert-amyl, n-hexyl, n-octyl, 2-ethylhexyl, 1,1,3,3-tetramethylbutyl, n-decyl or n-dodecyl.

Compounds which are very particularly preferred have the formula (I) in which R is H, $R^1$ is H, CH$_3$, C$_6$H$_5$, cyclohexyl, phenyl containing an alkyl group having 8 C atoms, or a group of the formula —CH$_2$—S—CH$_2$COOR$^6$, and $R^2$ is C$_6$H$_5$, naphthyl or phenyl containing an alkyl group having 8 C atoms, or $R^1$ and $R^2$, together with the nitrogen atom to which they are attached, form a radical of the formula (III) above, a is the number 1, $R^3$ is a radical of the formula —CH$_2$COOR$^6$ and $R^6$ is C$_8$-C$_{14}$alkyl or, for example, a mixture of C$_8$H$_{17}$isomers, and, in the formula (III), the two $R^5$s are H or octyl and X is —S—.

As $R^1$ and $R^2$, the phenyl containing an alkyl group having 8 C atoms is, for example, para-(1,1,3,3-tetramethylbutyl)phenyl.

As $R^5$, octyl is, for example, n-octyl and especially 2-ethylhexyl.

The compounds which are particularly preferred include those of the formulae:

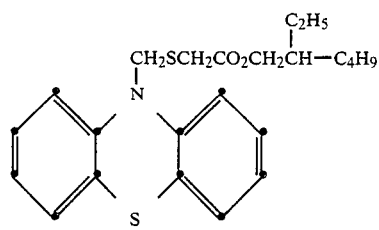

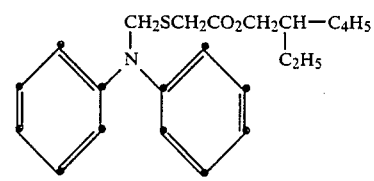

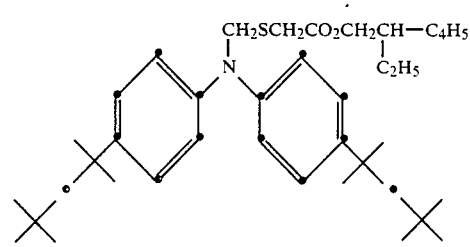

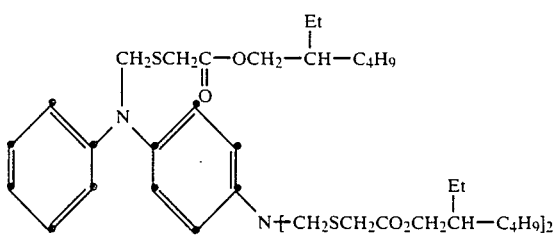

and

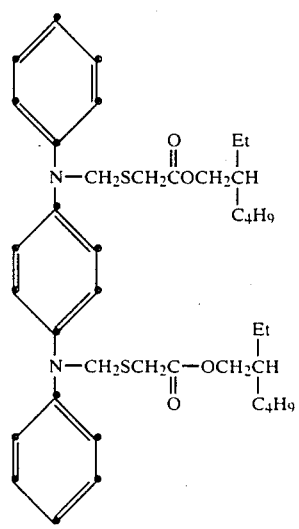

Compounds of the formula (I) in which R is H can, for example, be prepared by reacting a compound of the formula (IV)

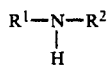  (IV)

in which $R^1$ and $R^2$ are as defined in the formula (I) with formaldehyde or a formaldehyde donor and with a compound of the formula (V)

$$R^3SH \quad (V)$$

in which $R^3$ is as defined in the formula (I).

The reaction can, for example, be carried out at temperatures from 15° C. to 220° C., in particular between 80° C. and 150° C., in the absence or presence of organic solvents.

Examples of suitable solvents are primary, secondary or tertiary alcohols having 1 to 10 C atoms, such as methanol, ethanol, n-propanol, isopropanol, n-butanol, sec-butanol, tert-butanol or n-pentanol, ketones, such as acetone, methyl ethyl ketone or cyclohexanone, glycols, such as ethylene glycol or diethylene glycol, and also ethers, such as tetrahydrofuran or dioxane, or glycol ethers, such as ethylene glycol monomethyl or dimethyl ether, ethylene glycol monoethyl or diethyl ether, diethylene glycol monomethyl ether and diethylene glycol monoethyl ether, and also dipolar, aprotic solvents, such as acetonitrile, benzonitrile, dimethylformamide, N,N-dimethylacetamide, nitrobenzene, N-methylpyrrolidone, aliphatic or aromatic hydrocarbons, such as hexane, methylene chloride, benzene or benzene which is substituted by alkyl, alkoxy or halogen, such as toluene, xylenes, anisole or chlorobenzene, or aromatic N-heterocyclic compounds, such as pyridine, picoline or quinoline, or mixtures of the above-mentioned solvents.

Paraformaldehyde or aqueous formaldehyde solutions, such as formalin, or hexamethylenetetramine (Urotropin) in the presence of a base, such as ammonia, can be used as formaldehyde or a formaldehyde donor.

Both formaldehyde and the compounds of the formula (V) can be employed in stoichiometric amounts or in excess. Thus they can, for example, be employed independently of one another in an amount of 2 to 10 moles, relative to 1 mole of the reactant of the formula (IV). If more than one NH group is present in the compound of the formula (IV), the molar ratios of the formaldehyde and the compound of the formula (V) should be adjusted accordingly.

In order to react the reactants with one another it is possible in principle initially to take all the components at a fairly low temperature and then to heat the mixture up to the region of the reaction temperature, or to add the individual components to one another in any desired sequence in the region of the reaction temperature. A further embodiment consists in initially taking the compound of the formula (IV) together with formaldehyde and metering in the compound of the formula (V) in the region of the reaction temperature. A further possible means consists in metering in simultaneously the compound of the formula (V) and formaldehyde into the compound of the formula (IV). It is entirely possible to carry out the process not only batchwise, but also continuously.

The compounds of the formula (I) in which $R^1$ is H, a is the number 1 and R is phenyl, naphthyl or $C_7$–$C_{30}$alkaryl can, for example, also be prepared by first preparing an aldimine of the formula (VI)

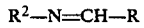  (VI)

by processes known per se by reacting an amine of the formula $R^2NH_2$ with an aldehyde of the formula O=CH—R, and then reacting the aldimine thus formed with a compound of the formula $HSR^3$ to give the compound of the formula (I), R, $R^2$ and $R^3$ being as defined above.

The compounds of the formula (I) in which R is H and $R^3$ is a radical of the formula —$(CH_2)_2OCOR^7$ can, for example, also be prepared by reacting a compound of the formula (VII)

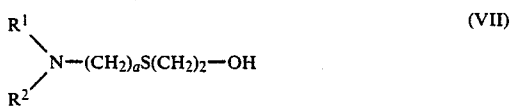  (VII)

by processes known per se with an acid chloride of the formula $R^7$—COCl, an acid of the formula $R^7$—COOH or a methyl ester of an acid of the formula $R^7$—COOCH$_3$, in which $R^1$, $R^2$, $R^7$ and a are as defined above.

The compounds of the formula (VII) can, for example, be prepared by reacting an amine of the formula

with formaldehyde and mercaptoethanol by processes known per se.

The compounds of the formula (I) in which a is the number 2 or 3 and R is H can, for example, also be prepared by a free-radical addition reaction, for example in the presence of catalysts or under irradiation, between a thio derivative of the formula (V) and a compound of the formula (VIII)

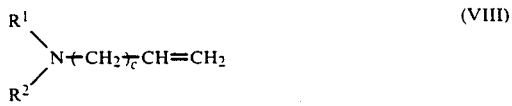  (VIII)

in which c is the number 0 or 1, $R^1$, $R^2$ and $R^3$ in the formulae (V) and (VIII) being as defined above.

Compounds of the formula (I) in which a is 2 or 3 and R is phenyl, naphthyl or $C_7$–$C_{30}$alkaryl can, for example, also be prepared by the same free-radical addition reaction described above.

The compounds of the formula (VIII) in which c is the number 1, can, for example, be prepared by subjecting a compound of the formula

to a condensation reaction with an allylbromide or chloride in the presence of a base, such as potassium hydroxide or sodium hydroxide or sodium methoxide. For example, in order to prepare the compounds of the formula (I) in which a is 3 and R is phenyl, naphthyl or $C_7$–$C_{30}$alkaryl, it is possible to employ an allyl bromide or chloride which is substituted by phenyl, naphthyl or $C_7$-$C_{30}$alkaryl.

Compounds of the formula (VIII) in which c is the number 0 can, for example, be prepared by reacting vinyl acetate with a compound of the formula $R^1$—N-H—$R^2$ in the presence of a suitable catalyst, for example mercury acetate, and sulfuric acid. The compounds of the formula (I) in which a is 2 and R is phenyl, naphthyl or $C_7$-$C_{30}$alkaryl can be obtained by the same reaction mentioned above from the vinyl acetate derivatives substituted by phenyl, naphthyl or $C_7$-$C_{30}$alkaryl.

The compounds of the formula (I) are excellently suitable for use as additives for lubricants and hydraulic fluids. The invention also relates, therefore, to the use of the compounds of the formula (I) as additives in lubricants and hydraulic fluids. The addition of the compounds according to the invention results in an improvement in the general performance characteristics, in particular the antioxidant, high-pressure and anti-wear properties. Since the compounds do not contain phosphorus, they are particularly suitable for engine oils, since it it is possible to avoid damaging the catalysts. In aqueous system there is a lower risk of attack by microorganisms as a result of the absence of phosphorus.

The compounds of the formula (I) are advantageously added to the lubricants and hydraulic fluids in an amount of 0.01 to 10% by weight, preferably in an amount of 0.05 to 5% by weight, relative to the lubricant or the hydraulic fluid. In organic systems it is advantageous to use 0.1 to 2% by weight and in aqueous systems it is advantageous to use 0.05 to 5% by weight.

Lubricant and hydraulic systems of this type can have a polar or non-polar nature. The selection criteria arise from the solubility properties of the corresponding compounds.

The lubricants which are suitable are familiar to those skilled in the art and are described, for example, in "Schmiermittel Taschenbuch" ("Lubricant Handbook") (Hüthig Verlag, Heidelberg, 1974) or by D. Klamann in "Schmierstoffe und verwandte Produkte" ("Lubricants and related products"), Verlag Chemie, Weinheim (1982).

Examples of these are lubricants and hydraulic fluids based on mineral oils or synthetic lubricants or hydraulic fluids, particularly those which are derivatives of esters of carboxylic acids and are used at temperatures of 200° C. and higher.

Examples of synthetic lubricants embrace lubricants based on a diester of a dibasic acid with a monohydric alcohol, for example dioctyl sebacate or dinonyl adipate, a triester of trimethylolpropane with a monobasic acid or with a mixture of such acids, for example trimethylolpropane tripelargonate, trimethylolpropane tricaprylate or mixtures thereof, a tetraester of pentaerythritol with a monobasic acid or with a mixture of such acids, for example pentaerythritol tetracaprylate, or a complex ester of monobasic and dibasic acids with polyhydric alcohols, for example a complex ester of trimethylolpropane wtih caprylic and sebacic acid or a mixture thereof.

Besides mineral oils, examples of particularly suitable products are poly-α-olefins, lubricants based on esters, phosphates, glycols, polyglycols and polyalkylene glycols, and mixtures thereof with water, and water itself, which preferably additionally contains a thickener as well in order to increase the viscosity.

The lubricants can, in addition, contain other additives which are added in order to improve the fundamental properties of lubricants even further. These include antioxidants, metal passivators, rust inhibitors, viscosity index improvers, pour-point depressants, dispersing agents, detergents, thickeners, biocides, antifoaming agents, deemulsifiers and emulsifiers and other high-pressure additives and friction reducers.

The concomitant use of diphenylamine additives of the formula

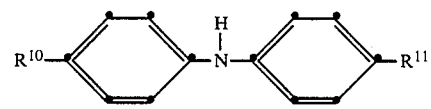

in which $R^{10}$ and $R^{11}$ independently of one another are H or $C_1$-$C_{12}$alkyl has proved particularly advantageous.

As $R^{10}$ and $R^{11}$, $C_1$-$C_{12}$alkyl can be linear or branched alkyl. Examples of these are the same examples which have already been indicated for the meaning of the radical $R^1$ as $C_1$-$C_8$alkyl, and also n-decyl and n-dodecyl.

The following are further examples of additional additives for lubricants and hydraulic fluids:

EXAMPLES OF THE PHENOLIC ANTIOXIDANTS

1. Alkylated monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, o-tert-butylphenol.

2. Alkylated hydroquinones 2,6-Di-tert-butyl-4-methoxyphenol, 2,5-di-tert-butylhydroquinone, 2,5-di-tert-amyl-hydroquinone, 2,6-diphenyl-4-octadecyloxyphenol.

3. Hydroxylated thiodiphenyl ethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidene-bisphenols 2,2'-Methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methylbenzyl)-6-tert-butyl-4-methyl-phenyl]terephthalate.

5. Benzyl compounds 1,3,5-Tri-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hyydroxybenzyl-mercaptoacetate, bis-(4-tert-butyl-3-hydroxy-2,6-dimethylbenzyl)dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzyl phosphonate, monoethyl 3,5-di-tert-butyl-4-hydroxybenzylphosphonate calcium salt.

6. Acylaminophenols

4-Hydroxy-lauranilide, 4-hydroxy-stearanilide, 2,4-bis-octylmercapto-6-(3,5-di-tert-butyl-4-hydroxyanilino)-s-triazine, octyl N-(3,5-di-tert-butyl-4-hydroxyphenyl)-carbamate.

7. Esters of β-(3,5-Di-tert-butyl-4-hydroxyphenyl)-propionic acid with monohydric or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol, bis-hydroxyethyloxamide.

8. Esters of β-(5-tert-butyl-4-hydroxy-3-methylphenyl)-propionic acid with monohydric or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol, di-hydroxyethyloxamide.

9. Amides of β-(3,5-Di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine, N,N'-bis-(3,5-di-tert-butyl-4-hydroxyphenylpropionyl)-hydrazine.

Examples of amine antioxidants

N,N'-Di-isopropyl-p-phenylenediamine, N,N'-di-sec-butyl-p-phenylenediamine, N,N'-bis-(1,4-dimethylpentyl)-p-phenylenediamine, N,N'-bis-(1-ethyl-3-methylpentyl)-p-phenylenediamine, N,N'-bis(1-methylheptyl)-p-phenylenediamine, N,N'-dicylcohexyl-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,-N'-di-sec-butyl-p-phenylenediamine diphenylamine, N-allyldiphenylamine, 4-isopropoxydiphenylamine, N-phenyl-1-naphthylamine, N-phenyl-2-naphthylamine, octylated diphenylamine, e.g. p,p'-di-tert-octyldiphenylamine, 4-n-butylaminophenol, 4-butrylaminophenol 4-nonanoylaminophenol, 4-dodecanoylaminophenol, 4-octadecanoylamino-phenol, di-(4-methoxyphenyl)-amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methyl-phenyl)-amino]-ethane, 1,2-di-(phenylamino)-propane, (o-tolyl)-biguanide, di-[4-(1',3'-dimethylbutyl)-phenyl]amine, tert-octylated N-phenyl-1-naphthylamine, mixture of monoalkylated and dialkylated tert-butyl-/tert-octyldiphenylamines, 2,3-dihydro-3,3-dimethyl-4H-1,4-benzothiazine, phenothiazine, n-allylphenothiazine.

Examples of other antioxidants

Aliphatic or aromatic phosphites, esters of thiodipropionic acid or of thiodiacetic acid, or salts of dithiocarbamic or dithiophosphoric acid.

Examples of metal deactivators, for example for copper, are

Triazoles, benzotriazoles and derivatives thereof, tolutriazoles and derivatives thereof, 2-mercaptobenzothiazole, 2-mercaptobenzotriazole, 2,5-dimercaptobenzothiadiazole, 2,5-dimercaptobenzotriazole, 5,5'-methylenebisbenzotriazole, 4,5,6,7-tetrahydrobenzotriazole, salicylidenepropylenediamine and salicylaminoguanidine and salts thereof.

Examples of rust inhibitors are:

(a) Organic acids, their esters, metal salts and anhydrides, e.g. N-oleoylsarcosine, sorbitanmonooleate, leadnaphthenate, alkenylsuccinicanhydride, e.g. dodecenylsuccinic anhydride, alkenylsuccinic acid partial esters and amides and 4-nonylphenoxy acetic acid.

(b) Nitrogen-containing compounds, e.g.

I. Primary, secondary or tertiary aliphatic or cycloaliphatic amines and amine salts of organic and inorganic acids, e.g. oil-soluble alkylammonium carboxylates.

II. Heterocyclic compounds, e.g. substituted imidazolines and oxazolines.

(c) Phosphorus-containing compounds, e.g.

Amine salts of phosphoric or phosphonic partial esters and zinc dialkyldithiophosphates (d) Sulfur-containing compounds, e.g.

Bariumdinonylnaphthalenesulfonates and calcium petroleumsulfonates

Examples of viscosity-index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylates and alkylated naphthalene derivatives

Examples of dispersants/surfactants are:

Polybutenylsuccinic acid amides or imides, polybutenylphosphonic acid derivatives and basic magnesium, calcium, and barium sulfonates and phenates.

Examples of anti-wear additives are:

Sulfur- and/or phosphorus- and/or halogen-containing compounds e.g. sulfurized vegetable oils, zinc dialkyldithiophosphates, tritolylphosphate, chlorinated paraffins, alkyl- and aryl disulfides and trisulfides, triphenylphosphorothionates, diethanolaminomethyltolutriazole and di-(2-ethylhexyl)-aminomethyltolutriazole.

The compounds of the formula (I) can also be used in accordance with the invention for stabilizing elastomers. Examples of elastomers are natural and synthetic rubbers and also mixtures thereof. The following are examples of elastomers:

Polydienes, for example polybutadiene, polyisoprene or polychloroprene; block polymers, for example styrene/butadiene/styrene, styrene/isoprene/styrene or acrylonitrile/butadiene copolymers;

Copolymers of monoolefins and diolefins with one another or with other vinyl monomers, for example ethylene/alkyl acrylate copolymers, ethylene/alkyl methacrylate copolymers, ethylene/vinyl acetate copolymers and terpolymers of ethylene with propylene and a diene, such as hexadiene, dicyclopentadiene or ethylidenenorbornene;

Halogen-containing polymers, for example polychloroprene, chlorinated rubber, chlorinated or chlorosulfonated polyethylene, epichlorohydrin homopolymers and copolymers, chlorotrifluoroethylene copolymers, polymers formed from halogen-containing vinyl compounds, for example polyvinylidene chloride or polyvinylidene fluoride; and copolymers thereof, such as vinyl chloride/vinylidene chloride, vinyl chloride/vinyl acetate or vinylidene chloride/vinyl acetate;

Polyurethanes derived on the one hand from polyethers, polyesters and pollybutadiene containing terminal hydroxyl groups, and, on the other hand, from aliphatic or aromatic polyisocyanates, and also precursors thereof;

Natural rubber;

Mixtures (polyblends) of the abovementioned polymers;

Aqueous emulsions of natural or synthetic rubbers, for example natural rubber latex, or latices of carboxylated styrene/butadiene copolymers.

If appropriate, these elastomers are in the form of latices and can be stabilized as such.

Preferred compositions are those containing, as the elastomer, a polydiene, such as polybutadiene rubber, a halogen-containing polymer, such as polyvinylidene fluoride, or a polyurethane.

The compounds of the formula (I) can, for example, be employed in an amount of 0.01–10% by weight, preferably 0.05–5.0% by weight, but very preferably 0.1–4.0% by weight, relative to the elastomer.

In addition to the compounds of the formula (I), the elastomers can contain other additives. Examples of additional additives are the additives already listed above under items 1 to 9, and also 10.1. Esters of β-(3,5-di-tert-butyl-4-hydroxyphenyl)-propionic acid with monohydric or polyhydric alcohols, e.g. with methanol, diethylene glycol, octadecanol, triethylene glycol, 1,6-hexanediol, pentaerythritol, neopentyl glycol, tris(hydroxyethyl)isocyanurate, thiodiethylene glycol and N,N'-bis(hydroxyethyl)oxalic acid diamide.

10.2. Esters of β-(5-tert-butyl-4-hydroxy-3-methylphenyl)-propionic acid with monohydric or polyhydric alcohols, e.g. with methanol, diethylene glycol, octadecanol, triethylene glycol, 1,6-hexanediol, pentaerythritol, neopentyl glycol, tris-(hydroxyethyl)isocyanurate, thiodiethylene glycol and N,N'-bis(hydroxyethyl)oxalic acid diamide.

10.3. Esters of β-(3,5-dicyclohexyl-4-hydroxyphenyl)-propionic acid with monohydric or polyhydric alcohols, e.g. with methanol, diethylene glycol, octadecanol, triethylene glycol, 1,6-hexanediol, pentaerythritol, neopentyl glycol, tris-(hydroxyethyl)isocyanurate, thiodiethylene glycol and N,N'-bis(hydroxyethyl)oxalic acid diamide.

10.4. Amides of β-(3,5-di-tert-butyl-4-hydroxyphenyl)-propionic acid e.g. N,N'-bis-(3,5-di-tert-butyl-4-hydroxyphenylpropionyl)-hexamethylenediamine, N,N'-bis(3,5-di-tert-butyl-4-hydroxyphenylpropionyl)-trimethylenediamine and N,N'-bis-(3,5-di-tert-butyl-4-hydroxyphenylpropionyl-hydrazine.

11. UV absorbers and light stabilizers 11.1. 2-(2'-Hydroxyphenyl)-benzotriazoles, for example the 5'-methyl, 3',5'-di-tert-butyl, 5'-tert-butyl, 5'-(1,1,3,3-tetramethylbutyl), 5-chloro-3',5'di-tert-butyl, 5-chloro-3'-tert-butyl-5'-methyl, 3'-sec-butyl-5'-tert-butyl, 4'-octyloxy, 3',5'-di-tert-amyl and 3',5'-bis-(α,α-dimethylbenzyl) derivatives.

11.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

11.3 Esters of substituted and unsubstituted benzoic acids, for example, 4-tert-butylphenyl salicylate, phenyl salicylate, octylphenyl salicylate, dibenzoylresorcinol, bis-(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

11.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbo-methoxy-β-cyanovinyl)-2-methylindoline.

11.5. Nickel compounds, for example nickel complexes of 2,2'-thio-bis-[4-(1,1,3,3-tetramethylbutyl)-phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monalkyl esters, e.g. the methyl or ethyl ester, nickel complexes of ketoximes, e.g. 2-hydroxy-4-methylphenyl undecyl ketoxime and nickel complexes of 1-phenyl-4-lauroyl-5-hydroxypyrazole, with or without additional ligands.

11.6. Sterically hindered amines, for example bis-(2,2,6,6-tetramethylpiperidyl)sebacate, bis-(1,2,2,6,6-pentamethylpiperidyl)sebacate, bis-(1,2,2,6,6-pentamethylpiperidyl)n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl)-1,2,3,4-butanetetraoate and 1,1'-(1,2-ethanediyl)-bis-(3,3,5,5-tetramethyl-piperazinone).

11.7. Oxalic acid diamides, for example 4,4'-dioctyloxyoxanilide, 2,2'-dioctyloxy-5,5'-di-tert-butyloxanilide, 2,2'-didodecyloxy-5,5-di-tert-butyloxanilide, 2-ethoxy-2'-ethyloxanilide, N,N'-bis(3-dimethylaminopropyl)-oxamide, 2-ethoxy-5-tert-butyl-2'-ethyloxanilide and its mixture with 2'-ethoxy-2'-ethyl-5,4'-di-tert-butyloxanilide and mixtures of ortho- and para-methoxy-disubstituted oxanilides and mixtures or ortho- and para-ethoxy-disubstituted oxanilides.

12. Metal deactivators, for example N,N'-diphenyloxamide, N-salicylal-N'-salicyloylhydrazine, N,N'-bis(salicyloyl)-hydrazine, N,N'-bis(3,5-di-tert-butyl-4-hydroxyphenylpropionyl)-hydrazine, 3-salicyloylamino-1,2,4-triazole and bis-(benzylidene)-oxalic acid dihydrazide.

13. Phosphites and phosphonites, for example triphenyl phosphite, diphenylalkyl phosphites, phenyldialkyl phosphites, tris-(nonylphenyl)phosphite, trilauryl phosphite, trioctadecyl phosphite, distearyl pentaerythritol diphosphite, tris-(2,4-di-tert-butylphenyl)phosphite, diisodecyl pentaerythritol diphosphite, bis-(2,4-di-tert-butylphenyl)pentaerythritol diphosphite, tristearyl sorbitol triphosphite, tetrakis-(2,4-di-tert-butylphenyl) 4,4'-biphenylene diphosphonite and 3,9-bis-2,4-di-tert-butylphenoxy)-2,4,8,10-tetraoxa-3,9-diphosphaspiro[5.5]undecane.

14. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide or pentaerythritol tetrakis-(β-dodecylmercapto)-propionate.

15. Polyamide stabilizers, for example, copper salts in combination with iodides and/or phosphorus compounds and salts of divalent manganese.

16. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, and antimony pyrocatecholate or zinc pyrocatecholate.

17. Nucleating agents, for example, 4-tert-butylbenzoic acid, adipic acid and diphenylacetic acid.

18. Fillers and reinforcing agents, for example, calcium carbonate, silicates, glass fibres, asbestos, talc, kaolin, mica, barium sulfate, metal oxides and hydroxides, carbon black and graphite.

19. Other additives, for example plasticizers, lubricants, emulsifiers, pigments, optical brighteners, flameproofing agents, antistatic agents and blowing agents.

The following examples illustrate the invention in greater detail. Parts and percentages are by weight, unless stated otherwise.

EXAMPLE 1

2-Ethylhexyl N,N-diphenylaminomethylthioacetate 33.9 g (0.2 mol) of diphenylamine, 40.9 g (0.2 mol) of 2-ethylhexyl thioglycollate and 6.6 g (0.22 mol) of paraformaldehyde are mixed in a sulfonation flask equipped with a reflux condenser and a mechanical stirrer (propeller stirrer ~350 r.p.m). The mixture is heated to 120° C. and is kept at this temperature (internal temperature) for 3 hours under a gentle stream of nitrogen. The resulting mixture is then cooled to 50° C., and 50 ml of toluene are added. The mixture is washed with twice 30 ml of water in a separating funnel. The organic phase is then concentrated on a rotary evaporator and the residue is dried for one hour at 80° C. in a high vacuum (4 Pa; 0.03 mmHg).

75,3 g ($\hat{=}$97.6% yield) of a slightly brown oil of the formula

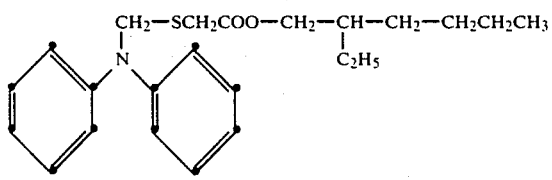

are obtained.

Analysis ($C_{23}H_{31}NO_2S$; molecular weight: 385.57):

| Calculated | | Found | |
|---|---|---|---|
| C | 71.65% | C | 71.5% |
| H | 8.10% | H | 8.2% |
| N | 3.63% | N | 3.6% |
| S | 8.32% | S | 8.4% |

EXAMPLE 2

N-(2-Ethylhexyloxycarbonylmethylthiomethyl)-phenothiazine

The procedure followed is analogous to the process indicated in Example 1 above, except that 33.9 g (0.2 mol) of thiodiphenylamine, 40.9 g (0.2 mol) of 2-ethylhexyl thioglycollate and 6.6 g (0.22 mol) of paraformaldehyde are reacted. 82.3 g (=99% yield) of a brown oil of the formula

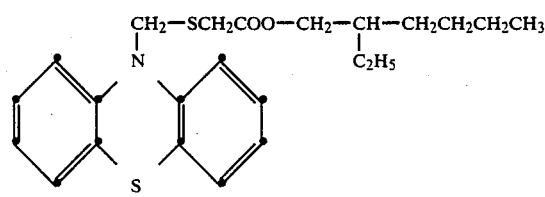

are obtained; this oil has the following combustion analysis:

Analysis ($C_{23}H_{29}NO_2S_2$; molecular weight: 451.61):

| Calculated | | Found | |
|---|---|---|---|
| C | 66.47% | C | 66.2% |
| H | 7.03% | H | 7.1% |
| N | 3.37% | N | 3.4% |
| S | 15.43% | S | 15.6% |

EXAMPLE 3

2-Ethylhexyl N-phenyl-N-naphthylaminomethylthioacetate

The procedure followed is analogous to the process indicated in Example 1 above, except that 43.9 g (0.2 mol) of N-phenyl-N-α-naphthylamine, 40.9 g (0.2 mol) of 2-ethylhexyl thioglycollate and 6.6 g (0.22 mol) of paraformaldehyde are reacted. 84.3 g (=96.8% yield) of a brown oil of the formula

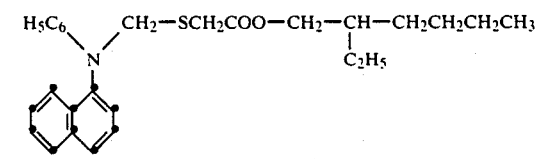

are obtained; this oil has the following combustion analysis:

Analysis ($C_{27}H_{33}NO_2S$; molecular weight: 435.63):

| Calculated | | Found | |
|---|---|---|---|
| C | 74.44% | C | 74.3% |
| H | 7.64% | H | 7.6% |
| N | 3.22% | N | 3.2% |
| S | 7.36% | S | 7.5% |

EXAMPLE 4

Methyl N,N-diphenylaminomethylthioacetate

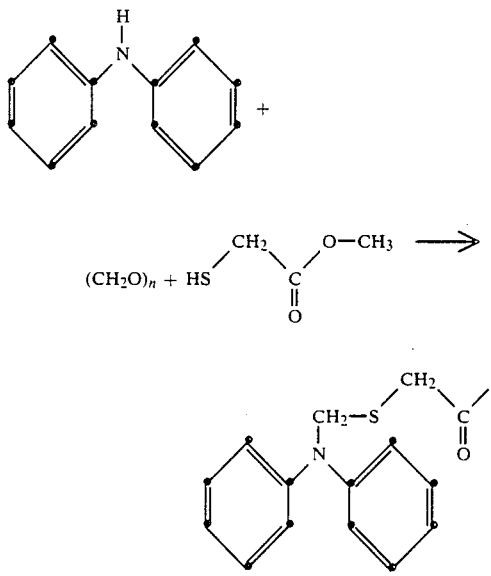

33.9 g (0.2 mol) of diphenylamine, 6.6 g (0.22 mol) of paraformaldehyde and 21.1 g (0.2mol) of methyl thioglycollate are reacted for 5 hours at 120° C., with stirring and under a gentle stream of nitrogen, in a 100 ml sulfonation flask equipped with a propeller stirrer, and the reaction mixture is then cooled to 80° C., taken up in 100 ml of toluene and washed with three times 50 ml of H$_2$O in a separating funnel. The organic phase is dried over 10 g of Na$_2$SO$_4$ and evaporated on a rotary evaporator, and the residue is dried at 80° C. for 1 hour under a high vacuum. This gives 56.9 g (99% of theory) of a brown oil.

Analysis: Found; C 66.7%, H 6.0%, N 4.9%, S 11.2%, Calculated; C 66.87%, H 5.96%, N 4.87%, S 11.16%.

EXAMPLE 5

2-Ethylhexyl N-naphthylamino-N,N-bis-(methylthioacetate)

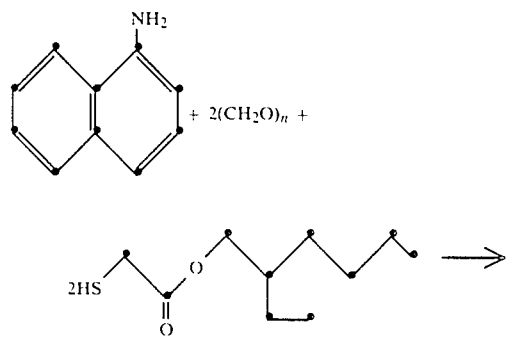

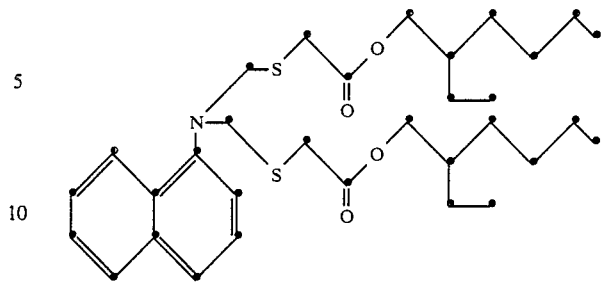

14.3 g (0.1 mol) of 1-naphthylamine, 6.6 g (0.22 mol) of paraformaldehyde and 40.8 g (0.2 mol) of 2-ethylhexyl thioglycollate are initially placed in a 350 ml sulfonation flask equipped with a propeller stirrer. The reaction mixture is reacted for 3 hours at 120° C., with stirring and under a gentle stream of nitrogen, cooled to 80° C., taken up in 200 ml of toluene and washed with three times 100 ml of H$_2$O in a separating funnel. The organic phase is dried over 10 g of Na$_2$SO$_4$, filtered and concentrated on a rotary evaporator, and the residue is dried at 80° C. for 2 hours under a high vacuum. 54.8 g (95% of theory) of a brown oil are obtained.

Analysis: Calculated; C 66.75%, H 8.58%, N 2.43%, S 11.14%, Found; C 66.9%, H 8.5%, N 2.3%, S 11.2%.

EXAMPLE 6

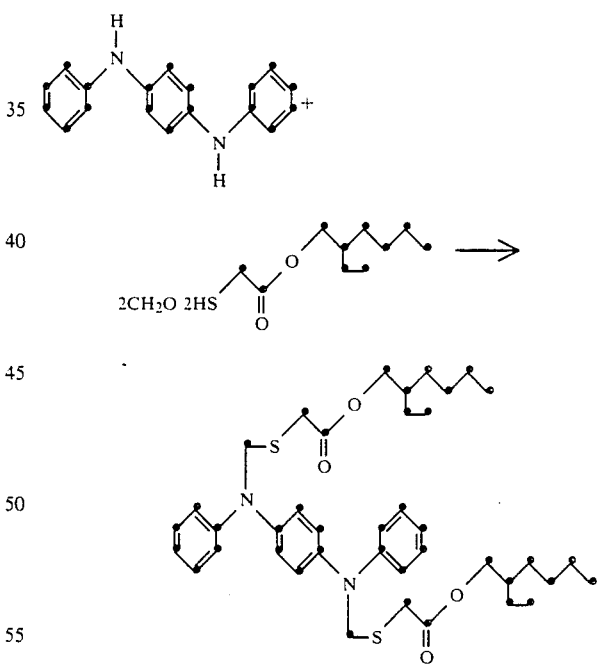

52.1 g (0.2 mol) of N,N'-diphenyl-1,4-phenylenediamine and 81.7 g (0.4 mol) of 2-ethylhexyl thioglycollate in 200 ml of ethanol are initially placed in a 750 ml sulfonation flask equipped with a propeller stirrer, and are heated to reflux temperature. 36.7 g (0.44 mol) of 36% aqueous formaldehyde are added dropwise in the course of 2 hours, and the reaction mixture is then boiled under reflux for 16 hours. The batch is concentrated on a rotary evaporator, and the residue is then dried at 80° C. for 2 hours under a high vacuum. 127.3 g (91.8% of theory) of a dark brown oil are obtained.

Analysis: Calculated; C 69.33%, H 8.15%, N 4.04%, S 9.25%, Found; C 70.2%, H 8.13%, N 3.96%, S 9.29%.

EXAMPLE 7

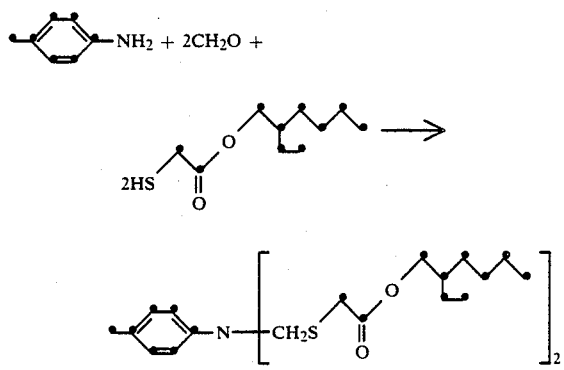

21.4 g (0.2 mol) of p-toluidine and 81.73 g (0.4 mol) of 2-ethylhexyl thioglycollate in 200 ml of alcohol are initially placed in a 750 ml sulfonation flask under a gentle stream of nitrogen, and are boiled under reflux. 36.7 g (0.44 mol) of 36% formaldehyde are added dropwise under these conditions in the course of 1 hour. The mixture is then boiled under reflux for 12 hours. The solution is concentrated on a rotary evaporator, and the residue is dried at 80° C. for 1 hour under a high vacuum. 104.5 g (96.8% of theory) of a slightly brown oil are obtained.

Analysis: Found; C 64.3%, H 9.1%, N 2.7%, S 12.0%, Calculated; C 64.52%, H 9.15%, N 9.15%, N 2.59%, S 11.88%.

EXAMPLE 8

Test of stabilization to oxidation (TFOUT test: thin-film oxygen uptake test)

This test is a modified version of the "rotary bomb oxidation test for mineral oils" (ASTM D 2272). It is described in detail in "C. S. Ku and S. M. Hsu, A Thin-Film Oxygen Uptake Test for the Evaluation of Automotive Crankcase Lubricants, *Lubrication Engineering*, volume 40 (2), 75-83 (1984)". The test oil used is a commercially available engine oil with a content of zinc dithiophosphate (ZDTP) formulated on a mineral oil basis and containing half the customary amount of zinc dithiophosphate (0.75%: zinc content 0.06%, relative to the engine oil); this alteration was made to make it possible to demonstrate a potential effect of the stabilizer to be tested.

The additives prepared in Examples 1-4 are tested in the engine oil described in the presence of 2% of a liquid, oxidized, nitrated fraction of a motor fuel as catalyst (concentration employed: 4%) and a liquid metal naphthenate as a further catalyst (concentration employed: 4%; water and the two liquid catalyst substances are supplied with a certificate of analysis under the standard reference material No. 1817 of the National Bureau of Standards (NBS). The test is complete when there is a marked kink in the pressure/time diagram. The results shown in the Table below indicate the time (in minutes) elapsed before the kink in the pressure time diagram.

Long times correspond to good stabilizing effectiveness of the additives.

Concentration of additive: 0.5% by weight, relative to the oil.

| Formulation | Induction period (time, in minutes, elapsed before marked decrease in pressure) |
| --- | --- |
| Oil | 76 |
| Oil + additive according to Example 1 | 140 |
| Oil + additive according to Example 2 | 116 |
| Oil + additive according to Example 3 | 141 |
| Oil + additive according to Example 4 | 160 |

EXAMPLE 9

Test of anti-wear protection

The ASTM Standard Method D 2783-81 using the Shell four-ball apparatus is employed to test for suitability for anti-wear protection. The base oil used is Catenex ® P 941 made by Shell. The following are determined:

(a) the weld load WL, as the load (in kg) at which the 4 balls weld together in the course of 10 seconds, and (b) the average wear scar diameter WSD at a load of 40 kg for 1 hour (in mm).

1% by weight of the additive is employed in all the test samples.

The results are shown in the Table.

| Additive from Example No. | WL (kg) | WSD (mm) |
| --- | --- | --- |
| No additive (comparison) | 160 | 0.90 |
| 1 | 180 | 0.60 |
| 4 | 200 | 0.52 |
| 5 | 200 | 0.55 |

EXAMPLE 10

Test of copper passivation

A brightly polished copper sheet measuring 60×10×1 mm is immersed in turbine oil containing 50 ppm of dissolved sulfur and also 0.05% of 3-[bis-(2'-ethylhexyl)-aminomethyl]-benzothiazolin-2-thione. A comparison sample contains no thiazoline derivative. The samples are heated at 100° C. for 2 hours. The copper sheet is then washed with petroleum ether and dried, and the colour of the sheet is assessed as specified in ASTM D 130 by comparison with a standard colour table. The assessment involves 4 stages:

1—no tarnish,
2—moderate tarnish,
3—considerable tarnish,
4—corrosion.

· Result: The colour of the sample containing the additive according to Example 1 is 1 (no tarnish).

EXAMPLE 11

Stabilization of polybutadiene rubber 100 parts of polybutadiene which has been prestabilized with 0.36% of 2,6-di-tert-butyl-p-cresol is additionally plasticized with 0.25% of the additive on a two-roller mill for 6 minutes at 50° C.

Panels 10 mm thick compressed at 60° C. from the rolled sheets. The panel without the compound according to the invention is prepared in the same way.

Testing for the effectiveness of the additive added is carried out by heat aging in a circulating air oven at 80° C. The criterion used is the gel content formed during ageing in the oven. The gel content increases rapidly after an induction period. The time after which a gel content of 5% is reached is used as an arbitrary definition of the induction period.

The gel content is determined as follows:

1 gram of the polybutadiene is dissolved in 100 ml of toluene at room temperature in the course of 12 hours. The solution is filtered through glass wool, and the filtered solution is evaporated to dryness. The gel content is given by:

$$\text{Gel} = \frac{E - A}{E} \times 100(\%)$$

where
E = sample weight (1 gram)
A = weight of residue from evaporation
The results are shown in the Table:

| Additive from Example (0.25%) | Treatment in an oven at 80° C., in number of weeks, until the gel content is 5% |
|---|---|
| Control (no additive) | 4 |
| 1 | 7 |
| 6 | 8 |
| 12* | 13 |

*A product of the formula

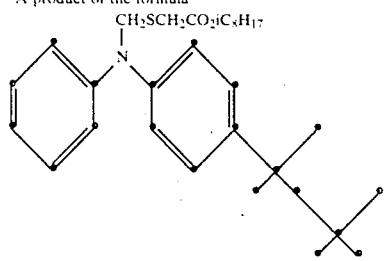

(2-Ethylhexyl(N—phenyl-N—p-isooctylphenyl)-aminomethylthioacetate), prepared by a process analogous to Example 1.

What is claimed is:

1. A compound of the formula (I)

 (I)

in which the Rs independently of one another are H, phenyl, naphthyl or $C_7$-$C_{30}$alkaryl and $R^1$ is H, $C_1$-$C_8$alkyl, $C_7$-$C_9$aralkyl, $C_5$-$C_{12}$cycloalkylphenyl, naphthyl, $C_7$-$C_{30}$alkaryl or a group of the formula (II)

—(CH$_2$)$_a$—SR$^3$ (II)

$R^2$ is $C_7$-$C_{30}$alkaryl, phenyl, naphthyl or phenyl containing an HO of $C_1$-$C_{18}$alkoxy group or a group of the formulae

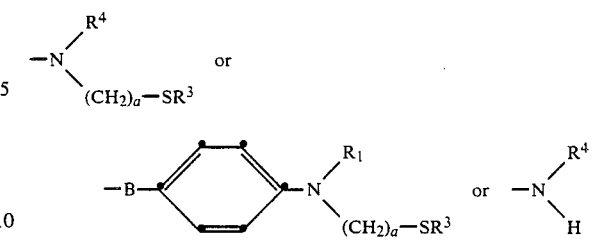

in the para-position, or $R^1$ and $R^2$, together with the nitrogen atom to which they are attached, are a radical of the formula (III)

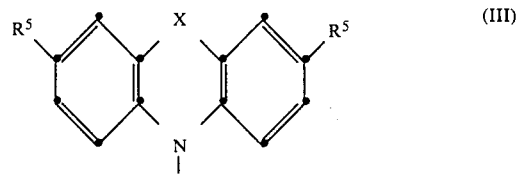 (III)

$R^3$ is a radical of the formulae —(CH$_2$)$_b$—COOR$^6$ or —(CH$_2$)$_2$OCOR$^7$, a is the number 1, 2 or 3 and b is the number 1 or 2, and $R^4$ is phenyl or a group of the formula (II), the two $R^5$s independently of one another are H, $C_1$-$C_{24}$alkyl, $C_5$-$C_{12}$cycloalkyl or $C_7$-$C_9$aralkyl, and $R^6$ is H, $C_1$-$C_{24}$-alkyl or benzyl, $R^7$ is $C_1$-$C_{14}$alkyl, phenyl or a group of the formula —(CH$_2$)$_m$—Y—(CH$_2$)$_m$—COO(CH$_2$)$_2$—S—(CH$_2$)$_a$N(R$^1$)(R$^2$)

in which Y is —O— or —S—, a is the number 1, 2 or 3 and m is the number 1 or 2, B is a direct bond, —S—, —S—S— or a $C_1$-$C_{12}$alkylene radical, X in the formula (III) is a direct bond, —S— or a group of the formulae

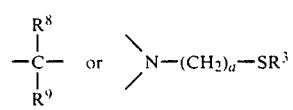

in which a and $R^3$ are as defined above, and $R^8$ and $R^9$ independently of one another are H, $C_1$-$C_8$alkyl or phenyl.

2. A compound of the formula (I) according to claim 1, in which R is H and $R^1$ is H, $C_1$-$C_{18}$alkyl, $C_7$-$C_{18}$alkaryl, cyclohexyl, phenyl, naphthyl or a group of the formula (II)

—(CH$_2$)$_a$—SR$^3$ (II)

$R^2$ is $C_7$-$C_{18}$alkaryl, phenyl, naphthyl or phenyl containing, in the para-position, an HO group of the formula

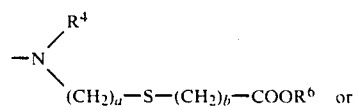

or $R^1$ and $R^2$, together with the nitrogen atom to which they are attached, are a radical of the formula (III) according to claim 1, $R^3$ is a radical of the formula —(CH$_2$)$_b$-COOR$^6$, a is the number 1 or 3 and b is the number 1 or 2, R$^4$ is phenyl or a group of the formula —(CH$_2$)$_a$—S(CH$_2$)$_b$-COOR$^6$ in which a and b are as defined in claim 2, R$^6$ is C$_1$-C$_{24}$alkyl, and, in the formula (III), the two R$^5$s are H, C$_1$-C$_{12}$alkyl or C$_9$phenylalkyl and X is —S—.

3. A compound of the formula (I) according to claim 1, in which R is H, R$^1$ is H, CH$_3$, C$_6$H$_5$, cyclohexyl, phenyl substituted by C$_4$-C$_{12}$alkyl, or a group of the formula —CH$_2$—S—CH$_2$—COOR$^6$, and R$^2$ is C$_6$H$_5$, naphthyl or phenyl substituted by C$_4$-C$_{12}$alkyl, or R$^1$ and R$^2$, together with the nitrogen atom to which they are attached, form a radical of the formula (III) according to claim 1, a is the number 1, R$^3$ is a radical of the formula —CH$_2$COOR$^6$ and R$^6$ is C$_4$-C$_{18}$alkyl, and, in the formula (III), the two R$^5$s are H or C$_4$-C$_8$alkyl and X is —S—.

4. A compound of the formula (I) according to claim 1, in which R is H, R$^1$ is H, CH$_3$, C$_6$H$_5$, cyclohexyl, phenyl containing alkyl group having 8 C atoms, or a group of the formula —CH$_2$—S—CH$_2$COOR$^6$, and R$^2$ is C$_6$H$_5$, naphthyl or phenyl containing an alkyl group having 8 C atoms, or R$^1$ and R$^2$, together with the nitrogen atom to which they are attached, form a radical of the formula (III) according to claim 1, a is the number 1, R$^3$ is a radical of the formula —CH$_2$COOR$^6$ and R$^6$ is C$_8$-C$_{14}$alkyl or a mixture of C$_8$-H$_{17}$ isomers, and, in the formula (III), the two R$^5$s are H or octyl and X is —S—.

5. A compositon containing
(a) at least one lubricant, one hydraulic fluid or one elastomer and
(b) 0.01-10% by weight, relative to the lubricant, the hydraulic fluid or to the elastomer, of at least one compound of the formula (I) according to claim 1.

6. A composition according to claim 5, wherein the component (a) is a lubricant.

7. A composition according to claim 5, wherein the component (a) is an elastomer.

8. A process for improving the stability and oxidation properties of lubricants, hydraulic fluids and elastomers which comprise incorporating into said lubricants, hydraulic fluids or elastomers an effective stabilizing amount of a compound corresponding to the formula (I)

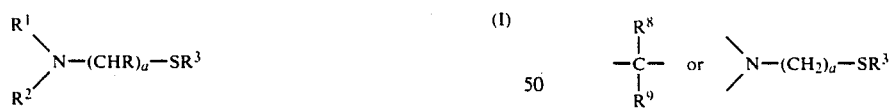

in which the Rs independently of one another are H, phenyl, naphthyl or C$_7$-C$_{30}$alkaryl and R$^1$ is H, C$_1$-C$_8$alkyl, C$_7$-C$_9$aralkyl, C$_5$-C$_{12}$cycloalkylphenyl, naphthyl, C$_7$-C$_{30}$alkaryl or a group of the formula (II)

—(CH$_2$)$_a$—SR$^3$ (II)

R$^2$ is C$_7$-C$_{30}$alkaryl, phenyl, naphthyl or phenyl containing an HO or C$_1$-C$_{18}$alkoxy group or a group of the formulae

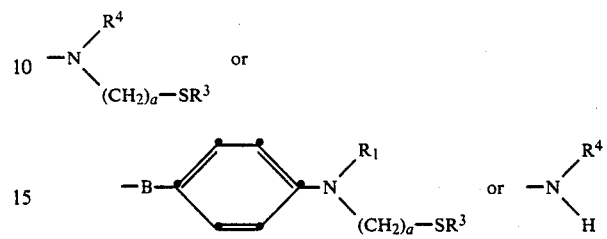

in the para-position, or R$^1$ and R$^2$, together with the nitrogen atom to which they are attached, are a radical of the formula (III)

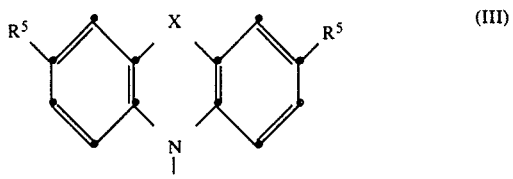

R$^3$ is a radical of the formulae —(CH$_2$)$_b$—COOR$^6$ or —(CH$_2$)$_2$OCOR$^7$, a is the number 1, 2 or 3 and b is the number 1 or 2, and R$^4$ is phenyl or a group of the formula (II), the two R$^5$s independently of one another are H, C$_1$-C$_{24}$alkyl, C$_5$-C$_{12}$cycloalkyl or C$_7$-C$_9$aralkyl, and R$^6$ is H, C$_1$-C$_{24}$-alkyl or benzyl, R$^7$ is C$_1$-C$_{14}$alkyl, phenyl or a group of the formula —(CH$_2$)$_m$—Y—(CH$_2$)$_m$—COO(CH$_2$)$_2$—S—(CH$_2$)$_a$N(R$^1$)(R$^2$)

in which Y is —O— or —S—, a is the number 1, 2 or 3 and m is the number 1 or 2, B is a direct bond, —S—, —S—S— or a C$_1$-C$_{12}$alkylene radical, X in the formula (III) is a direct bond, —S— or a group of the formulae

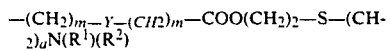

in which a and R$^3$ are as defined above, and R$^8$ and R$^9$ independently of one another are H, C$_1$-C$_8$alkyl or phenyl.

* * * * *